United States Patent [19]

Ling et al.

[11] Patent Number: 5,598,341
[45] Date of Patent: Jan. 28, 1997

[54] REAL-TIME IN-LINE DEFECT DISPOSITION AND YIELD FORECASTING SYSTEM

[75] Inventors: Zhi-Min Ling; Thao Vo; Siu-May Ho; Ying Shiau, all of San Jose; Yeng-Kaung Peng, Saratoga; Yung-Tao Lin, Fremont, all of Calif.

[73] Assignee: Advanced Micro Devices, Inc., Sunnyvale, Calif.

[21] Appl. No.: 401,490

[22] Filed: Mar. 10, 1995

[51] Int. Cl.$^6$ .................................................. G06F 19/00
[52] U.S. Cl. ................ 364/468.17; 364/490; 364/468.28
[58] Field of Search ............................ 364/468, 488–491, 364/578, 550, 551.01, 552, 554, 468.01, 468.17, 468.28; 437/7, 8

[56] References Cited

U.S. PATENT DOCUMENTS

| | | | |
|---|---|---|---|
| 3,751,647 | 8/1973 | Maeder et al. | 364/552 X |
| 4,849,804 | 7/1989 | Mader | 357/85 |
| 5,450,326 | 9/1995 | Black | 364/468 |
| 5,475,695 | 12/1995 | Caywood et al. | 364/468 X |

OTHER PUBLICATIONS

"Wafer Defect Data Management: An On–line Client–server Solution" by Ying Shiau, Bill Funsten and Tho Le La (Advanced Micro Devices) and Michael Laine (Inspex, Inc.), Semiconductor International, May 1995.

"A Simple New Yield Model" by W. Maly, H. T. Heineken, and F. Agricola, Semiconductor International, Jul. 1994.

Primary Examiner—Joseph Ruggiero

[57] ABSTRACT

A real-time in-line defect disposition and yield forecasting system for a semiconductor wafer having layer containing devices includes an in-line fabrication inspection tool, a design review station, and a yield management station. The in-line fabrication inspection tool inspects at least two layers of the semiconductor wafer and produces first information including particle size, particle location and number of particles introduced therein for each of these layers. The design review station inspects the layers of the semiconductor wafer and produces second information including layouts of each of the layers. The yield management station is operatively connected to the in-line fabrication inspection tool and to the design review station. The yield management station retrieves the first information and the second information from the in-line fabrication inspection tool and from the design review station. The yield management station determines at least one of a number of killer defects for the devices in each of the layers or a defect sensitive area index for each of the layers using the first and second information. The yield management station also determines a priority for analyzing each of the at least two layers responsive to at least one of the number of killer defects and the defect sensitive area index for each of the layers.

17 Claims, 9 Drawing Sheets

REAL-TIME IN-LINE DEFECT DISPOSITION AND YIELD FORECASTING SYSTEM

BACKGROUND OF THE INVENTION

1. Technical Field

The present invention generally relates to semiconductor wafer manufacture in the presence of particle contamination, and more particularly to the field of in-line defect disposition and yield forecasting in a real-time semiconductor wafer manufacturing environment.

2. Background of the Related Art

Currently, various wafer inspection and failure analysis tools are available which provide detailed qualitative and quantitative information regarding failures and processing defects which are experienced by semiconductor wafers and devices embedded therein. The qualitative and quantitative information is typically isolated or segregated in accordance with a specific inspection and analysis tool. Efforts have been made to display the outputs of the different wafer analysis tools together so that engineers can view the results of the different analysis tools to analyze the various defects encountered by a semiconductor wafer.

The problem of displaying various information output from different wafer analysis tools is exacerbated by the fact that most wafer analysis tools collect, process, and store data in a proprietary fashion. Accordingly, data can not be easily retrieved and displayed together. As a result, engineers are generally forced to use one wafer inspection and analysis tool at a time. The engineer must then transfer the semiconductor wafer from inspection tool to inspection tool.

Figure 1:
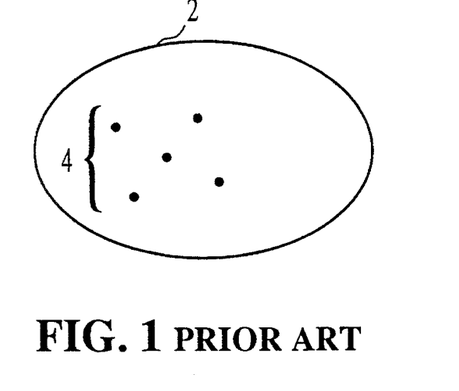
FIG. 1 is an illustration of a semiconductor wafer with a small particle count.
Figure 2:
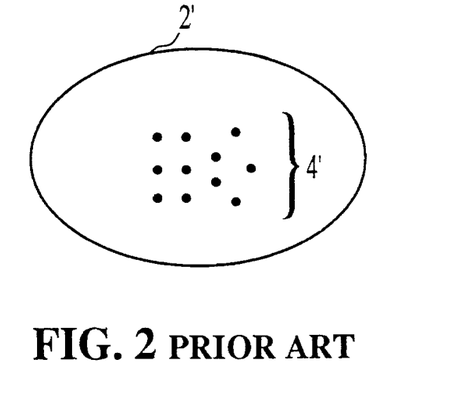
FIG. 2 is an illustration of a semiconductor wafer with a high particle count.

For example, in-line defect measurement instruments have been used to count the total number of external particles introduced into the semiconductor wafer as a result of the inherent fallibilities of the manufacturing process. If one semiconductor wafer is discovered to have experienced contamination by more particles than other semiconductor wafers, the semiconductor wafer with the highest particle count will typically be assigned the highest priority for defect analysis and disposition. FIGS. 1–2 illustrate such a situation where semiconductor wafer 2 contains five particles 4, and semiconductor wafer 2' contains eleven particles 4'. Under this scenario, semiconductor wafer 2' would be given a higher priority with respect to defect analysis and disposition than semiconductor wafer 2.

Hence, based on the above, one step in the manufacture of a semiconductor wafer includes inspection and analysis to determine the origination of causes of defects in accordance with the number of particles discovered on the semiconductor wafer. However, not all particles introduced into the semiconductor devices will cause defects. Therefore, analyzing semiconductor wafers with more particles thereon may not produce dramatic increases in device yield. It also tends to overestimate particle-caused yield loss. Thus, much labor may be unnecessarily expended without any substantial increase in device yield.

Figure 3:
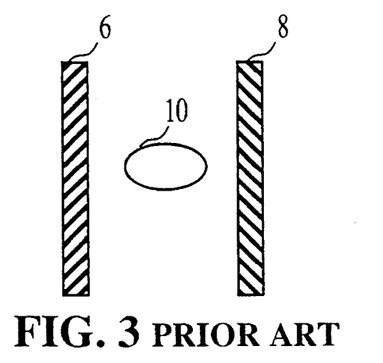
FIG. 3 is an illustration of a portion of a semiconductor device where no killer defects are experienced.
Figure 4:
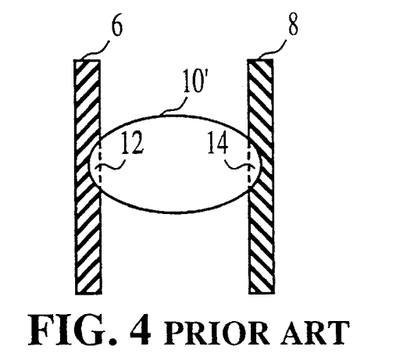
FIG. 4 is an illustration of a portion of a semiconductor device which has experienced a killer defect.

For example, FIGS. 3–4 illustrate a second method of analyzing a semiconductor wafer to determine whether to inspect and analyze it for defects. As shown in FIG. 3, a schematic illustration of a portion of a semiconductor device in a semiconductor wafer, circuit conductor lines 6 and 8 are designed in the semiconductor wafer to conduct electrical signals independently of one another. Due to imperfections in the semiconductor wafer manufacturing process, particle 10 has been introduced between conductors 6 and 8. Particle 10 does not interfere with either of conductors 6 and 8 and will generally not affect the functionality (or yield) of the semiconductor device or wafer. Accordingly, even though particle 10 is a result of a defect in the semiconductor wafer manufacturing process, the particle does not cause failure in the semiconductor device by disturbing signals flowing in conductors 6 and 8.

FIG. 4 is also a schematic illustration of a portion of a semiconductor device similar to the illustration of FIG. 3. However, in FIG. 4, particle 10' is much larger than particle 10 of FIG. 3. In this example, particle 10' is in contact with both conductors 6 and 8 at regions 12 and 14, respectively. If particle 10' is able to conduct electricity, the independent operation of conductors 6 and 8 will be jeopardized, creating cross-talk between conductors 6 and 8. If different devices are connected to conductors 6 and 8, a single particle 10' may destroy two devices embedded in the semiconductor wafer. Accordingly, particle 10' is what is commonly known as a "killer defect" since particle 10' may kill or prevent the normal operation of the semiconductor device which utilizes conductors 6 and 8. While the presence or absence of killer defects may be determined, this knowledge has not been utilized in any practical method of analyzing the defect characteristics of a semiconductor wafer. In addition, the presence or absence of killer defects has not been utilized in any practical method for in-line wafer defect disposition which involves the specific type of defect to be analyzed and the decision to scrap a wafer with too many defects.

Figure 5:
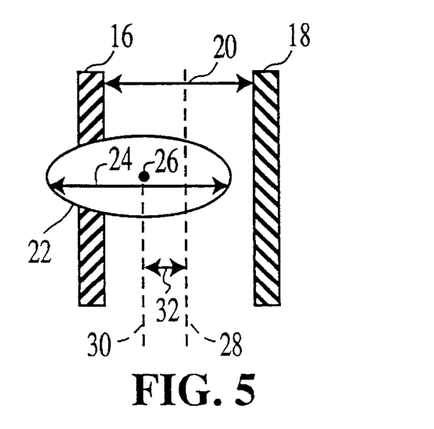
FIG. 5 is an illustration of a semiconductor device describing the relationship of the center of the particle and the center of the device conductors when no killer defect is present.
Figure 6:
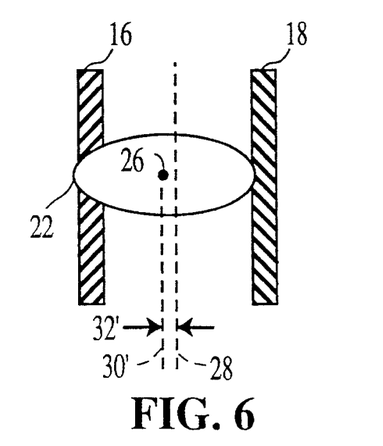
FIG. 6 is an illustration of a semiconductor device describing the relationship between the center of the particle and the center of the device conductors when a killer defect is present.

FIGS. 5 and 6 are schematic illustrations of a portion of a semiconductor device for providing some additional background information regarding semiconductor defects. In FIG. 5, semiconductor device conductor lines 16 and 18 are separated by the distance 20. During the manufacturing process, particle 22 is introduced in the semiconductor wafer due to manufacturing defects or imperfections. Particle 22 has a diameter 24 and center point 26 as illustrated. In the situation illustrated in FIG. 5, particle 22 is in contact only with conductor 16 and is unable to extend to be in contact with both conductors 16 and 18. Therefore, particle 22 is considered to be a non-killer defect. Note that in this situation, the position of center 26 of particle 22, identified by dashed line 30, is spaced apart from center position 28 of conductors 16 and 18 by distance 32. As particle 22 moves closer toward conductor 18, the center 26 of particle 22 will also move closer to the center 28 of conductors 16 and 18. FIG. 6 illustrates this situation.

As shown in FIG. 6, the center 26 of particle 22 has moved closer to the center 28 of conductors 16 and 20. This is illustrated by the distance between center 28 and center line 30' being 32' which is smaller than the distance 32 in FIG. 5. Particle 22 is in contact with both conductors 16 and 20, and is therefore considered a killer defect. Thus, as the center 26 of particle 22 is moved closer to center 28 of conductors 16 and 20, the particle 22 will become more likely a killer defect. This, of course, presumes that particle 22 is large enough to be in simultaneous contact with both conductors 16 and 20.

Figure 7:
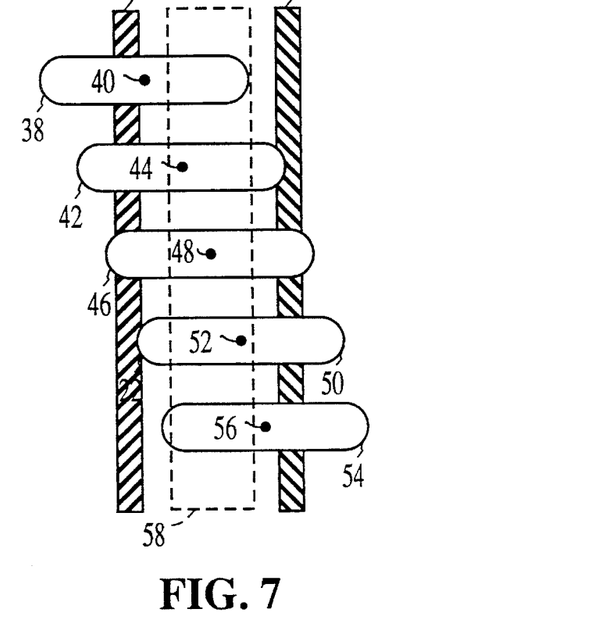
FIG. 7 is an illustration of a portion of a semiconductor device describing the sensitive area for a single particle size.

FIG. 7 is a schematic illustration of a semiconductor wafer where several particles have been introduced therein. As shown in FIG. 7, each of the particles 38, 42, 46, 50 and 54 are all of the same size. In addition, particle 38 has a center 40, particle 42 has a center 44, particle 46 has a center 48, particle 50 has a center 52, and particle 54 has center 56. The particles 38, 42, 46, 50 and 54 are positioned across device conductors 34 and 36 in such a manner as to illustrate the sensitive area of a semiconductor device for a specific particle size.

The sensitive area is defined as the area between two independent conductors which contains the center point of a killer defect particle. That is, when the center of a particle of sufficient diameter is located in the sensitive area, the particle will be a killer defect. Thus, particles 42, 46 and 50 are all killer defect particles, and therefore, define the width of sensitive area 58. Since particles 38 and 54 are not killer defect particles, the sensitive area boundaries are located between center 40 of particle 38 and center 44 of particle 42, and also between center 52 of particle 50 and center 56 of particle 54. The height of sensitive area 58 is defined by the height of conductors 34 and 36. Accordingly, FIG. 7 illustrates a sensitive area 58 for a given particle size, indicating that when the center of the particle is within the sensitive area, the particle will be a killer defect.

Figure 8:
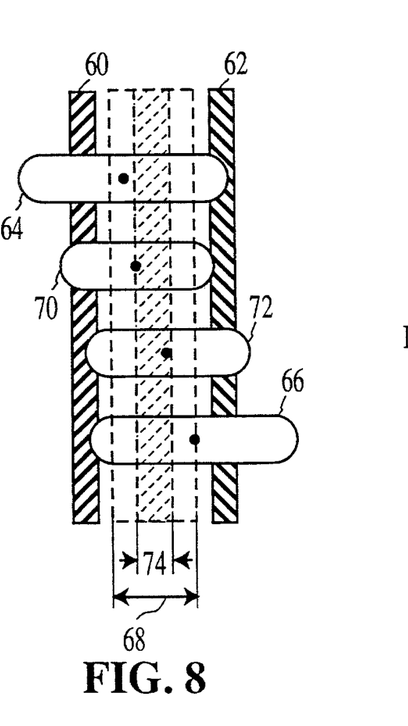
FIG. 8 is an illustration of a portion of a semiconductor device illustrating different sensitive areas for different particle sizes.

FIG. 8 is a schematic diagram of a semiconductor wafer illustrating different sensitive areas for different particle sizes. Particles 64 and 66 are of equal size. In addition, particles 70 and 72 are of the same size, but smaller than particles 64 and 66. All particles 64, 66, 70 and 72 are defect killer particles since all of the particles are in contact with both device conductors 60 and 62 causing device failure. For the larger particles 64 and 66, the width of the sensitive area is defined by distance 68 between the centers of the these particles. Similarly, for the smaller particles 70 and 72, the sensitive area width is defined by the distance 74 between centers of particles 70 and 72. As is clearly illustrated in FIG. 8, the smaller the particle size, the smaller the sensitive area width, and conversely, the larger the particle size the larger the sensitive area width. The sensitive area width will reach a maximum threshold and saturate when half the width of the particle is greater than the distance between conductors 60 and 62.

Figure 9:
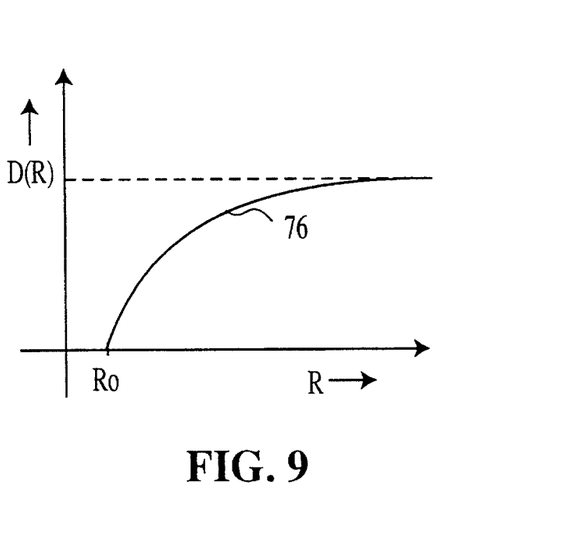
FIG. 9 is a diagram illustrating the relationship between sensitive area as a function of particle size.

FIG. 9 is a graphical illustration of the defect sensitive area D(R) as a function of the particle size R. As shown in FIG. 9, the initial particle size Ro reflects the smallest particle size which can be considered a killer defect, i.e., smallest particle size which will extend across and contact both conductors of semiconductor device. Curve 76 illustrates that as the particle size increases, the sensitive area will ultimately saturate and remain constant. While many have recognized these dynamics of the sensitive area in relation to the particle size, this information has not been used in such a manner which assists in the determination of whether a particular semiconductor wafer requires inspection and analysis, particularly in manufacturing environments where such decisions must be made quickly and efficiently. In addition, the sensitive area has also not been used in connection with in-line defect disposition.

Figure 10:
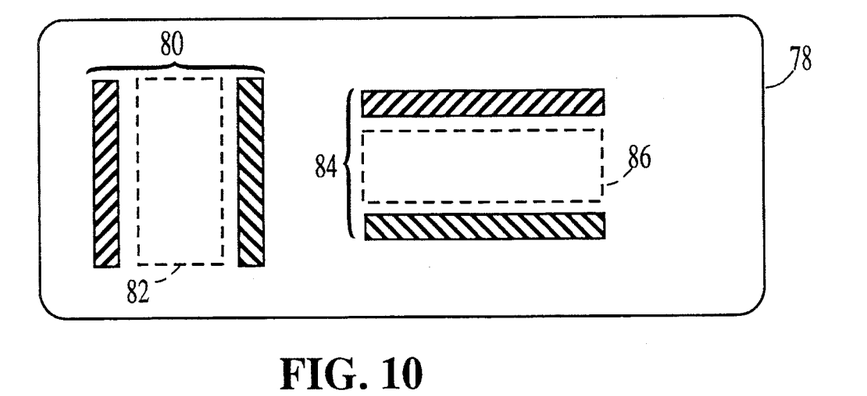
FIGS. 10 and 11 are schematic diagrams of a semiconductor wafer illustrating different sensitive area characteristics.
Figure 11:
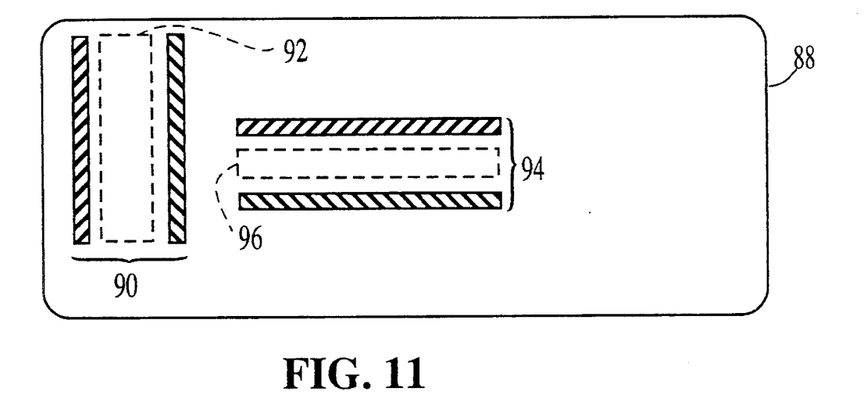

FIGS. 10 and 11 are schematic diagrams of portions of different semiconductor wafers showing different sensitive areas. As illustrated in FIG. 10, semiconductor wafer 78 includes a sensitive area 82 in semiconductor device 80, and includes sensitive area 86 in semiconductor device 84. FIG. 11 shows that semiconductor wafer 88 includes sensitive area 92 in semiconductor device 90, and includes a sensitive area 96 in semiconductor device 94. As can be seen in FIGS. 10 and 11, semiconductor wafer 78 has a larger combined sensitive area 82 and 86 than the combined sensitive areas 92 and 94 of semiconductor wafer 88. As described previously, a larger sensitive area will permit larger particles to be introduced into the semiconductor device without causing failures. Accordingly, one method of determining whether the semiconductor wafer should be inspected and analyzed would be to select the semiconductor wafer of the smallest combined sensitive areas. The semiconductor wafer with the smallest combined sensitive areas would be more sensitive to smaller particles than would semiconductor wafers of larger combined sensitive areas. Therefore, semiconductor wafer 88 may be considered as being the wafer which needs to be closely scrutinized. However, this method does not consider whether the semiconductor is actually experiencing significant defects, and therefore, inspection of a semiconductor wafer with the smallest sensitive areas may not necessarily dramatically increase device yield. In addition, this method considers only the combined sensitive area and does not consider the relative size of the individual sensitive areas.

Figure 12:
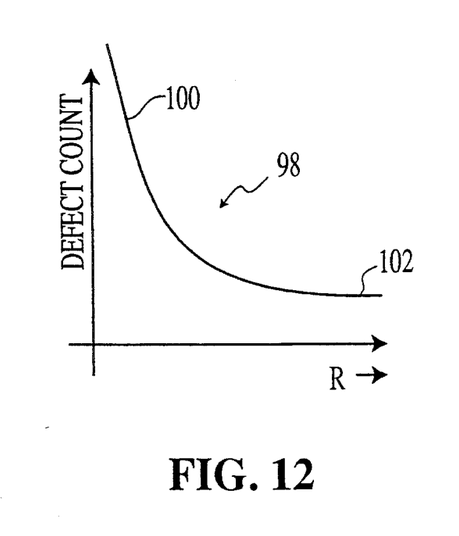
FIG. 12 is a diagram illustrating the relationship between the particle size and defect count.

Another item of information which may be collected regarding the characteristics of the semiconductor wafer relates to what is called the "wafer index." To understand the wafer index, the relationship between defect count and particle size is described. FIG. 12 is a diagram illustrating the relationship between particle size and defect count. A semiconductor wafer having small particles will tend to have a higher defect count as shown at 100, than a semiconductor wafer which experiences particles of larger size for the same area of the semiconductor wafer which is shown at 102. The overall curve 98, therefore, illustrates the basic relationship that, as particle size increases, the defect counts for the number of particles which are introduced into the semiconductor wafer will decrease. Accordingly, the defect count is inversely proportional to the size of particle size, i.e., $$\text{Defect count} \propto \frac{1}{\text{particle size } (R)}.$$

Figure 13:
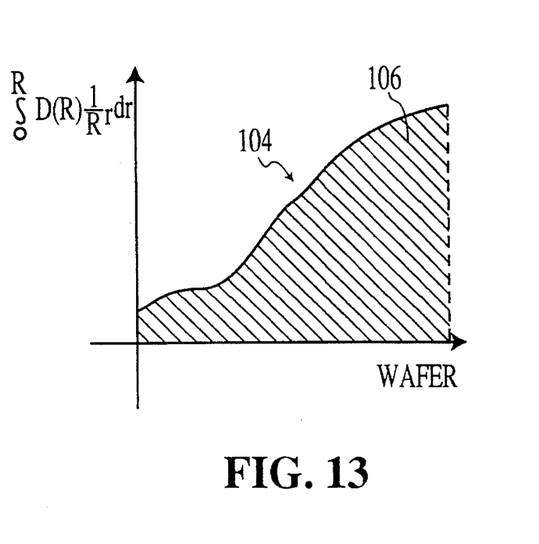
FIG. 13 is a diagram illustrating the relationship of the defect sensitive wafer index.

Curve 98 may be integrated with respect to particle size and sensitive area as shown in FIG. 13. FIG. 13 illustrates as 104 the integration of curve 98 of FIG. 12 with respect to particle size. Area 106 represents the defect sensitive area index for the wafer, where the $$\text{index} = \int_O^R D(R) \frac{1}{R^r} dr.$$

The higher the defect sensitive area index for the wafer, the more sensitive the semiconductor is to defects. Accordingly, the semiconductor wafer having a high defect sensitive area index may be selected for inspection and analysis. However, simply because one semiconductor wafer has a higher index than another does not necessarily provide detailed defect information that may be compared between wafers.

We have discovered, however, that the above methods of analyzing a semiconductor wafer to determine whether a wafer should be inspected and analyzed are deficient for several reasons. For example, simply counting the number of particles on the semiconductor wafer is no indication of whether these particles have actually caused device or circuit failure or the amount circuit failures experienced, as many of these particles may be non-killer defects. In this situation, the semiconductor circuits will still function in accordance with their original design. Thus, these in-line particle counts tend to overestimate the yield loss of devices in a semiconductor wafer, and unnecessary inspection and analysis is wasted on semiconductor wafers not experiencing serious problems.

We have further discovered since different semiconductor wafers have different integrated masking layouts, the defect sensitive area layouts will vary from wafer to wafer. Further, simply using the defect sensitive areas as an indication of which semiconductor wafer needs to be inspected may not be an appropriate gauge to compare a mature semiconductor product with a new product. For example, a mature product may already have undergone a significant amount of evaluation and optimization, and therefore, the mature product should perhaps be examined based on criteria other than simply the sensitive area criteria which ignores the product characteristics.

We have also discovered that determining which semiconductor requires defect reduction cannot be based merely on the highest number of in-line particle counts. As described above, even though a semiconductor wafer has many particle counts, these particle counts may not necessarily be killer defects which require immediate attention. Therefore, prioritizing the semiconductor wafers based on the highest number of particle counts may be inappropriate.

Finally, we have discovered that merely combining or adding all of the sensitive areas of the entire semiconductor wafer as another approach for determining whether the semiconductor wafer should be inspected and analyzed is also inefficient. This method does not take into account whether these defect sensitive areas are in fact experiencing defects. Thus, the semiconductor wafer with the most defect sensitive areas may not necessarily be the semiconductor wafer which is experiencing the most failures. For example, consider the situation where a semiconductor wafer has many defect sensitive areas which are much larger than the defect sensitive areas of another semiconductor wafer. The second semiconductor wafer with the smaller sensitive areas may experience more failures since in this case the smaller particle counts are the more likely to be killer defects.

Accordingly, it is desirable to determine not only the semiconductor wafer which is likely to experience more defects than other semiconductor wafers, but also the semiconductor wafer which is most likely to experience the greatest number of device defects.

It is further desirable to be able to determine not only the semiconductor wafer which is most likely to experience device losses, but also the specific layer of the semiconductor wafer which is likely to have the highest number of device losses. It is further desirable to determine the specific layers of the semiconductor wafer which are most likely to experience device losses in an automated and efficient manner to facilitate use of this information in a real-time manufacturing process.

It is also desirable to obtain the above information relating to device defects associated with a specific layer as well as the semiconductor wafer as a whole for various particle sizes.

It is further desirable to integrate in an efficient manner the information which is typically collected from the various wafer inspection tools. For example, it is desirable to integrate the particle count information which is generally determined using one inspection machine with sensitive area information which is generally collected using a second inspection machine.

SUMMARY OF THE INVENTION

It is therefore a feature and advantage of the present invention to provide a practical solution to identifying a semiconductor wafer and specific layer of the semiconductor wafer which requires inspection and analysis. As part of this solution, it is a feature and advantage of the present invention to determine the specific semiconductor wafer and layer in the wafer which requires inspection and analysis in a fast and efficient manner which is compatible with a real-time manufacturing process.

The present invention is based, in part, on the identification of the problem which has resulted in the inability to properly select the specific semiconductor wafer and layer which requires inspection and analysis. Accordingly, many semiconductor devices have experienced failures and have not been inspected and evaluated. Conversely, many semiconductor device layers and wafers are being inspected and analyzed, only to find that no substantial problems are being experienced, It is another feature and advantage of the present invention to identify the specific layer of the semiconductor wafer which is experiencing the highest number of device losses, It is also desirable to obtain the above information relating to device defects associated with a specific semiconductor layer and wafer with respect to different particle sizes.

It is another feature and advantage of the present invention to integrate the information which is generated by different wafer inspection machines in an efficient manner in order to efficiently and accurately determine or approximate the semiconductor layer and wafer which is experiencing significant device defects.

The present invention is able to provide an inspection and analysis technique and system which is able to efficiently identify the specific layer in a semiconductor wafer which is likely to experience significant device failures, as well as the semiconductor wafer which is likely to experience the most device failures overall. Since the present invention is able to quickly and efficiently identify the semiconductor layer and wafer which are likely to experience the most device failures, the present invention is able to inspect, analyze and correct the device failures much faster than any other technique or system.

To achieve these and other features and advantages of the present invention, a real-time in-line defect disposition and yield forecasting system for a semiconductor wafer having layers each with devices is provided. The real-time in-line defect disposition and yield forecasting system includes an in-line fabrication inspection tool, a design review station, and a yield management station. The in-line fabrication inspection tool inspects at least two layers of the semiconductor Wafer and produces first information including particle size, particle location and number of particles introduced therein for each of the at least two layers. The design review station inspects the at least two layers of the semiconductor wafer and produces second information including layouts of each of the at least two layers. The yield management station is operatively connected to the in-line fabrication inspection tool and to the design review station. The yield management station retrieves the first information and the second information from the in-line fabrication inspection tool and from the design review station. The yield management station determines at least one of a number of killer defects for the devices in each of the at least two layers or a defect sensitive area index for each of the at least two layers using the first and second information. The yield management station also determines a priority for analyzing each of the at least two layers responsive to at least one of the number of killer defects and the defect sensitive area index for each of the at least two layers.

In another embodiment of the invention, a real-time in-line defect disposition and yield forecasting method for a semiconductor wafer having layers each with devices is provided. The method includes the steps of inspecting at least two layers of the semiconductor wafer and producing first information including particle size, particle location and number of particles introduced therein for each of the at least two layers, and inspecting the at least two layers of the semiconductor wafer and producing second information including layouts of each of the at least two layers. In addition, the method includes the steps of retrieving the first and second information, and determining rat least one of a number of killer defects for the devices in each of the at least two layers and a defect sensitive area index for each of the at least two layers responsive to the first and second information. The method also includes the step of determining a priority for analyzing each of the at least two layers responsive to at least one of the number of killer defects and the defect sensitive area index for each of the at least two layers.

These together with other objects and advantages which will be subsequently apparent, reside in the details of construction and operation as more fully herein described and claimed, with reference being had to the accompanying drawings forming a part hereof wherein like numerals refer to like elements throughout.

DESCRIPTION OF THE PREFERRED EMBODIMENTS OF THE INVENTION

Figure 14A:
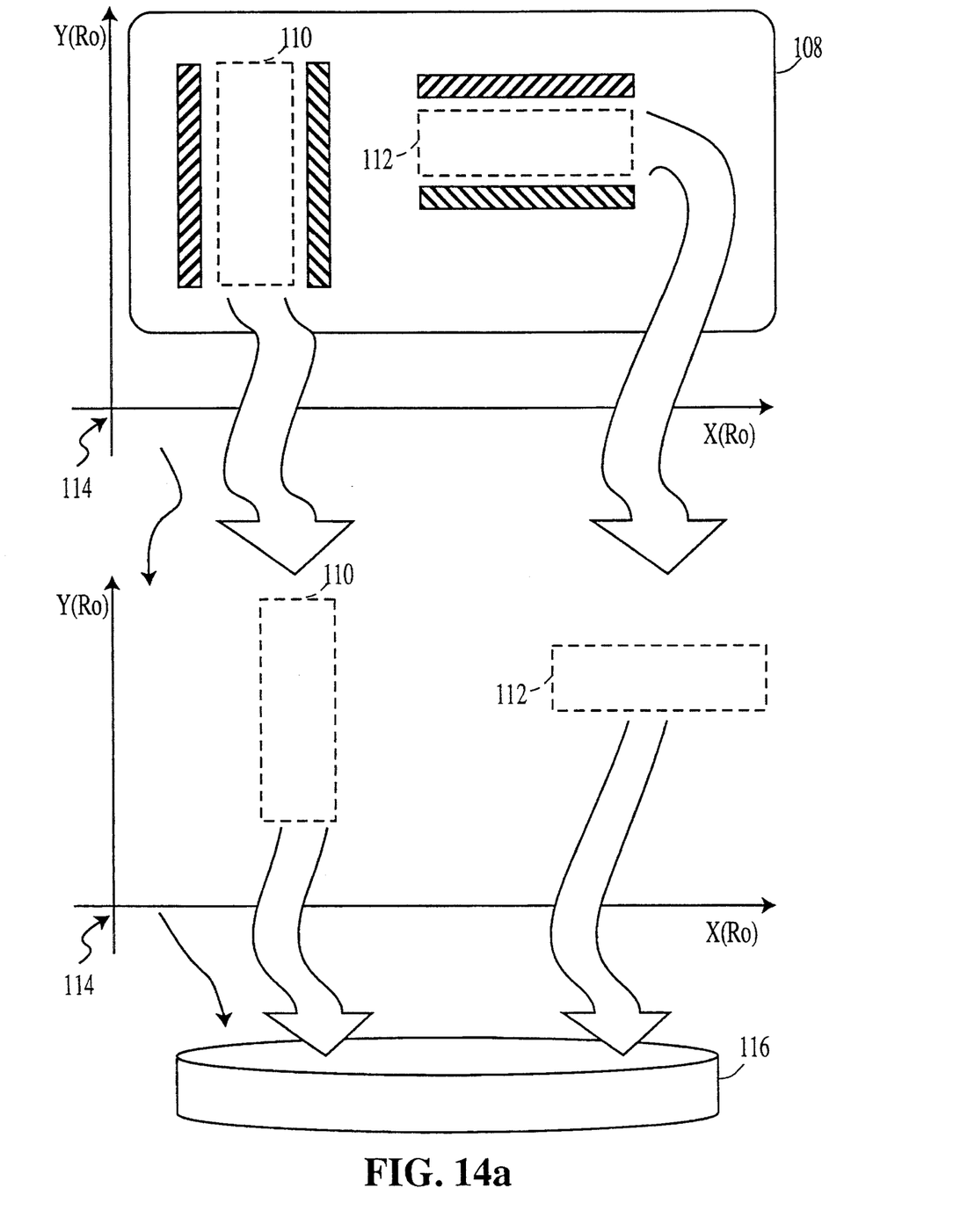
FIG. 14a is a schematic diagram illustrating the extraction and storage of sensitive area information.
Figure 14B:
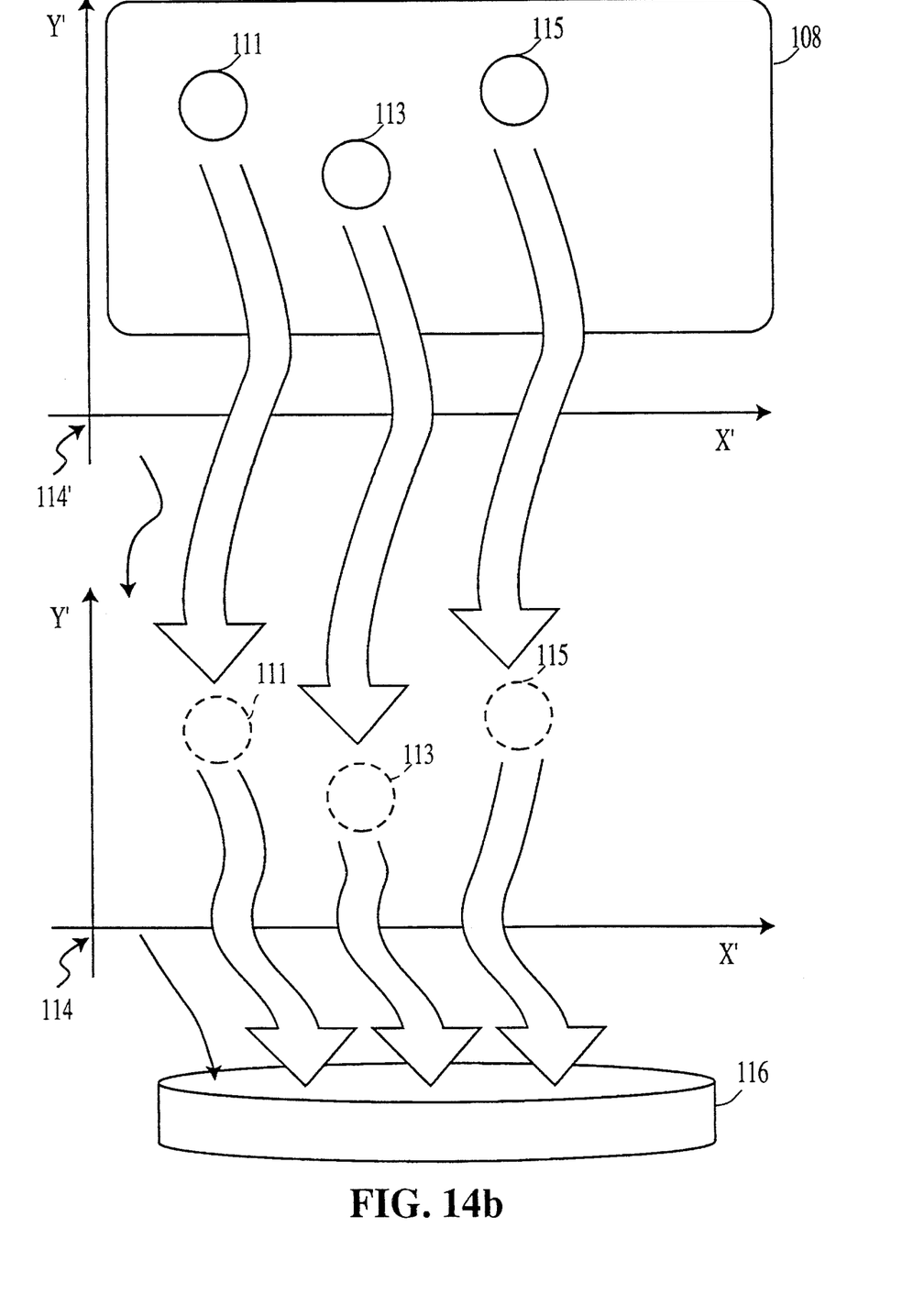
FIG. 14b is a schematic diagram illustrating the extraction and storage of particle size and location information.

The real-time in-line defect disposition and yield forecasting system herein recognizes the various disadvantages of the above mentioned techniques, and instead, determines whether a specific layer in a semiconductor device should be inspected and analyzed with respect to wafer disposition based on criteria which are specific to each of the different semiconductor layers. FIGS. 14a–14b are schematic diagrams illustrating the general principles of the real-time in-line defect disposition and yield forecasting system. As shown in FIG. 14a, the sensitive areas 110 and 112 are determined for a specific layer of the semiconductor wafer 108. These sensitive areas are determined based upon a reference particle size, such as the smallest particle size which is discernable by the inspection machines. Sensitive areas 110 and 112 are determined in accordance with a standard orientation axis 114. The information relating to sensitive areas 110 and 112 with respect to the orientation axis 114 is then extracted from the semiconductor layer and stored in database 116. This type of information is typically gathered by a standard design review station, described in connection with FIG. 19, which stores the various different mask layouts for each layer in the semiconductor wafer.

FIG. 14b illustrates a similar process for obtaining the various defect sizes and locations of semiconductor wafer 108. As shown in FIG. 14b, particles 111, 113, and 115 are detected with respect to orientation axis 114' which has a predetermined relationship with the orientation axis 114 discussed in connection with FIG. 14a. The particle information including size and location is then extracted from semiconductor wafer 108, and stored preferably in the same database 116. A standard in-line fabrication machine, described in connection with FIG. 19, collects this information. Thus, the real-time in-line defect disposition and yield forecasting system advantageously collects the various information relating to the sensitive area size and location and defect size and location to be used in combination as described below.

In addition to the advantage of mapping or plotting the particle size and location against the sensitive areas extracted from each layer of the semiconductor wafer, the real-time in-line defect disposition and yield forecasting system also includes the ability to alter or adapt the sensitive areas selected by the design stations in accordance with the predetermined particle size determined by the in-line fabrication equipment. As indicated previously, the design stations collect sensitive area information for each layer of the, semiconductor wafer in accordance with a predetermined particle size. If the defect disposition and yield forecasting system collects particle sizes which are different than the predetermined particle size gathered by the design stations, the defect disposition and yield forecasting system automatically converts the stored sensitive areas into sensitive areas which are appropriate for the different or actual particle size.

Figure 15:
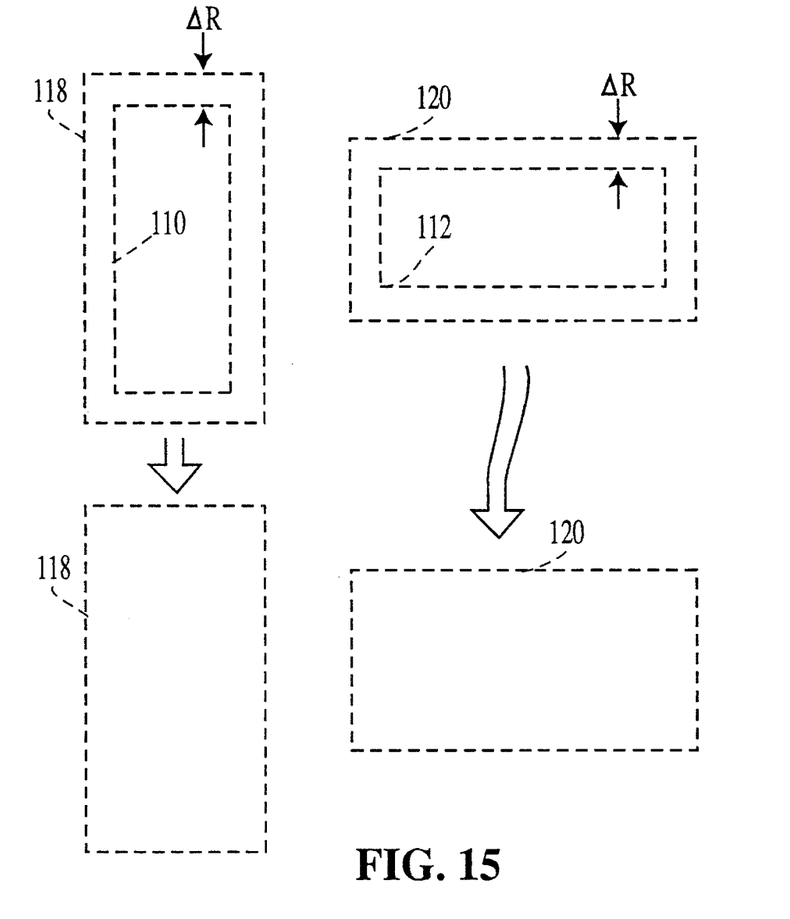
FIG. 15 is a diagram illustrating a relationship between sensitive area and particle size.

FIG. 15 illustrates the converting of one sensitive area with respect to one particle size into a second sensitive area having a different particle size. As shown in FIG. 15, sensitive areas 110 and 112 have been stored with respect to reference particle size Ro for a given layer. Ro may vary depending on the coordinate location of each layer in the semiconductor wafer. When the defect disposition and yield forecasting system determines particles having sizes which are different than Ro have been detected for a particular semiconductor layer, the defect disposition and yield forecasting system automatically converts the sensitive areas 110 and 112 into sensitive areas 118 and 120 in accordance with the specific particle size which was previously gathered by the in-line fabrication equipment. For example, assume particles of size R1 have been collected. The change in particle size, $\Delta R = (R1-Ro)/2$. Having computed the change in particle size, the defect sensitive areas 110 and 112 can be proportionally enlarged to correspond to the larger particle size R1 in an efficient manner as shown in FIG. 15 by defect sensitive areas 118 and 120.

Figure 16:
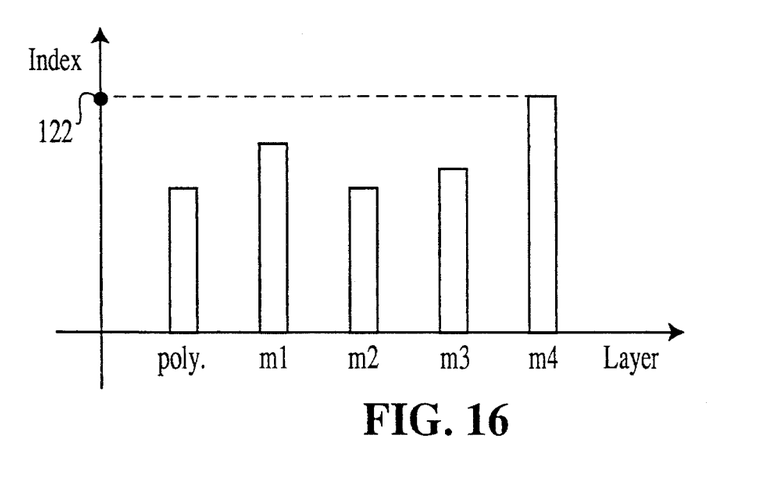
FIG. 16 is a diagram illustrating the defect sensitive area index for each of the layers of the semiconductor wafer.

The defect disposition and yield forecasting system also includes the ability to determine the defect sensitive area index for each layer in the semiconductor wafer as illustrated in FIG. 16. As discussed above, since the defect disposition and yield forecasting system is able to store the various sensitive areas on a per layer basis, each layer of the semiconductor wafer may be analyzed against another, as well as against layers of other semiconductor wafers. Thus, the layer having the highest defect sensitive area index will preferably be inspected and analyzed first since this layer is likely experiencing more device defects than other layers. For example, layer M4 in FIG. 16 has the highest defect sensitive area index 122, and therefore, is preferably inspected before the other semiconductor layers.

Figure 17:
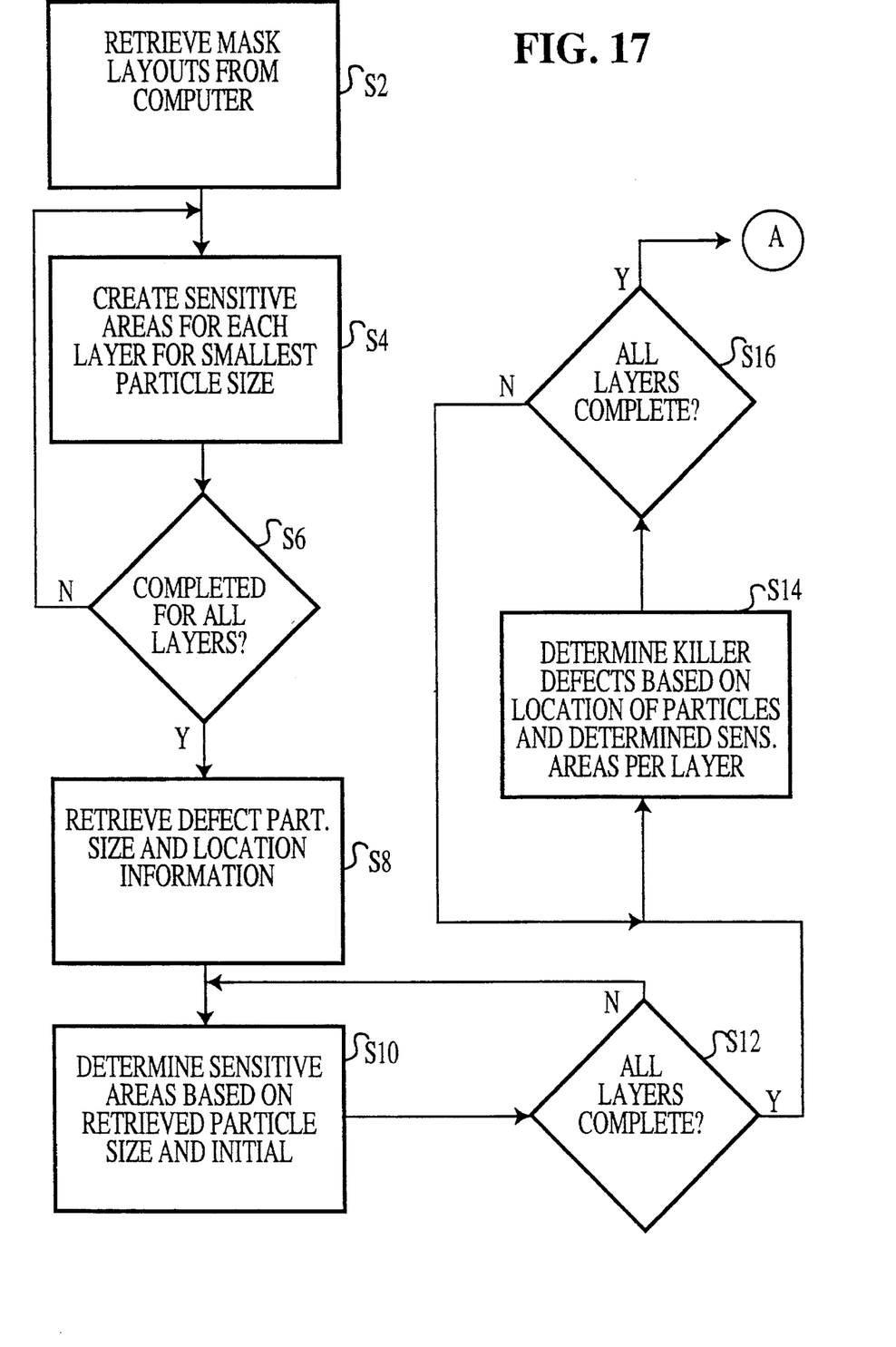
FIGS. 17–18 are flow charts illustrating the basic real-time in-line defect disposition and yield forecasting system process.
Figure 18:
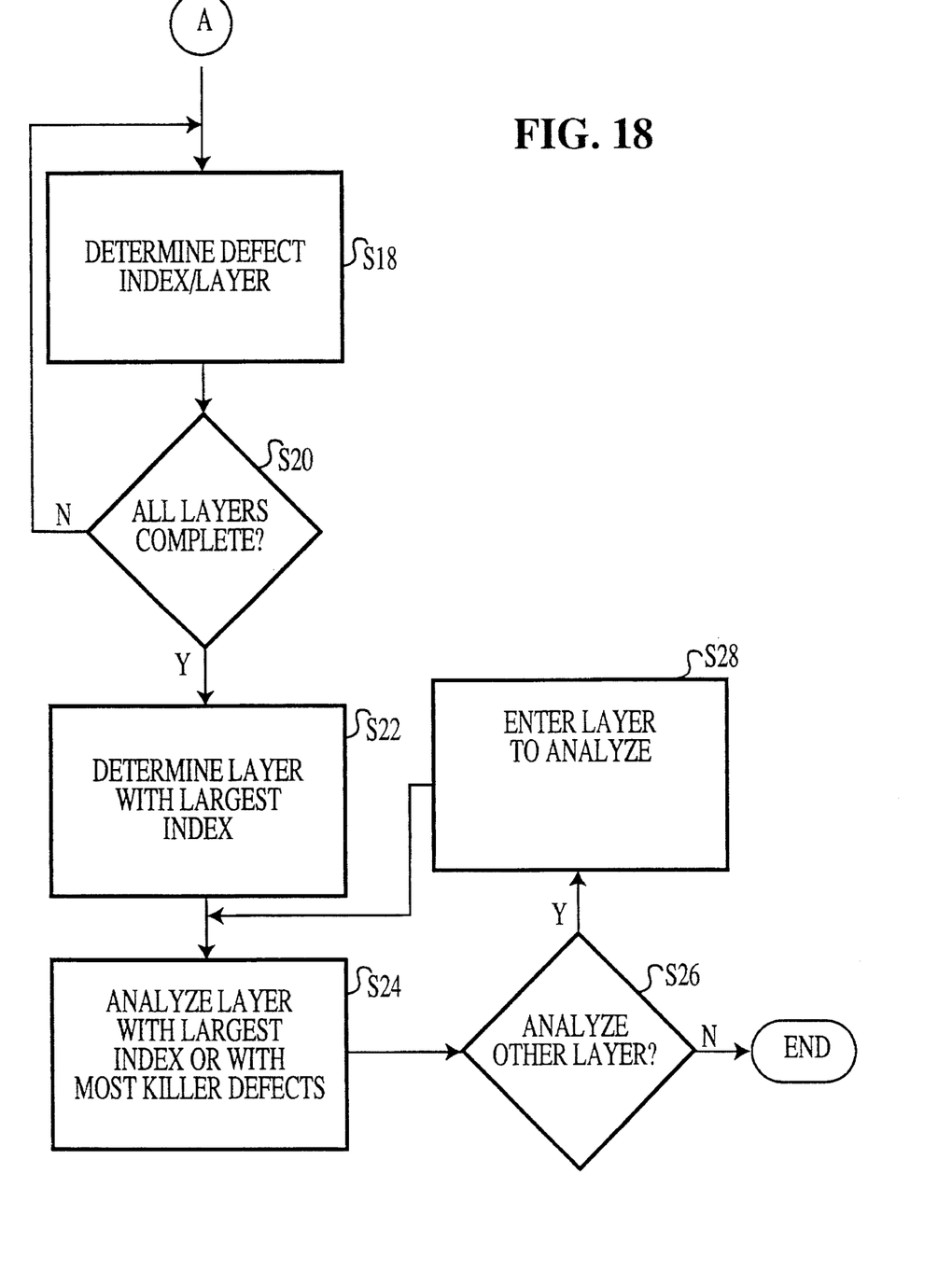

FIGS. 17–18 are flow charts illustrating the basic process steps of the real-time in-line defect disposition and yield forecasting system. As illustrated in FIG. 17, the defect disposition and yield forecasting system first retrieves the mask layouts from the database storing the various layouts which were extracted by the design station equipment in step S2. The defect disposition and yield forecasting system then creates sensitive areas for each of the different layers in accordance with a reference particle size in step S4. Preferably, the reference particle size is the smallest particle size which is discernable to the in-line fabrication equipment discussed below. The defect disposition and yield forecasting system then determines whether or not the sensitive areas have been created for each of the layers extracted by the design station equipment in step S6, and if not, returns to step S4.

When all sensitive areas have been created for all the layers in the semiconductor wafer under examination, the defect disposition and yield forecasting system retrieves the defect particle size and location information extracted by the in-line fabrication equipment from an associated data base in step S8. Next, in step S10, the defect disposition and yield forecasting system determines the sensitive areas for the specific layer based on the retrieved particle size and the initial sensitive areas previously determined in step S4. The defect disposition and yield forecasting system then determines whether the new sensitive areas have been created for all the layers in step S12, and if not, returns to step S10.

When all the new sensitive areas have been determined for each of the layers, the defect disposition and yield forecasting system then determines killer defects based on the location of the particles and the determined sensitive areas for each layer in step S14. Next, the defect disposition and yield forecasting system determines whether the killer defects have been determined for each of the layers in step S16, and if not, returns to step S14. When killer defects have been determined for all the layers, the defect disposition and yield forecasting system determines the defect sensitive area index or each layer in step S18. When it is determined that the defect sensitive area index is computed for each of the layers in step S20, the defect disposition and yield forecasting system determines the layer with the largest defect sensitive area index in step S22. In step S24, the defect disposition and yield forecasting system analyzes the layer with the largest defect sensitive area index or the layer with the most killer defects in step S24 which was determined previously. Other methods of prioritizing which semiconductor wafer and layer which are to be inspected might include particle count combined with either or both the killer defect count and the defect sensitive area index. The number of sensitive areas and sizes thereof may also be combined with one or more items of the above information.

After completing analysis of the layer, such as viewing various defect locations associated with the semiconductor wafer, the defect disposition and yield forecasting system then queries whether another layer is to be analyzed in step S26, for example, the layer with the second largest number of killer defects. If no additional layer is to be analyzed then the process ends, and if an additional layer is to be analyzed the user is prompted for next layer to analyze in step S280 Control is returned from step S28 to step S24 for additional analysis of the next semiconductor layer.

Figure 19:
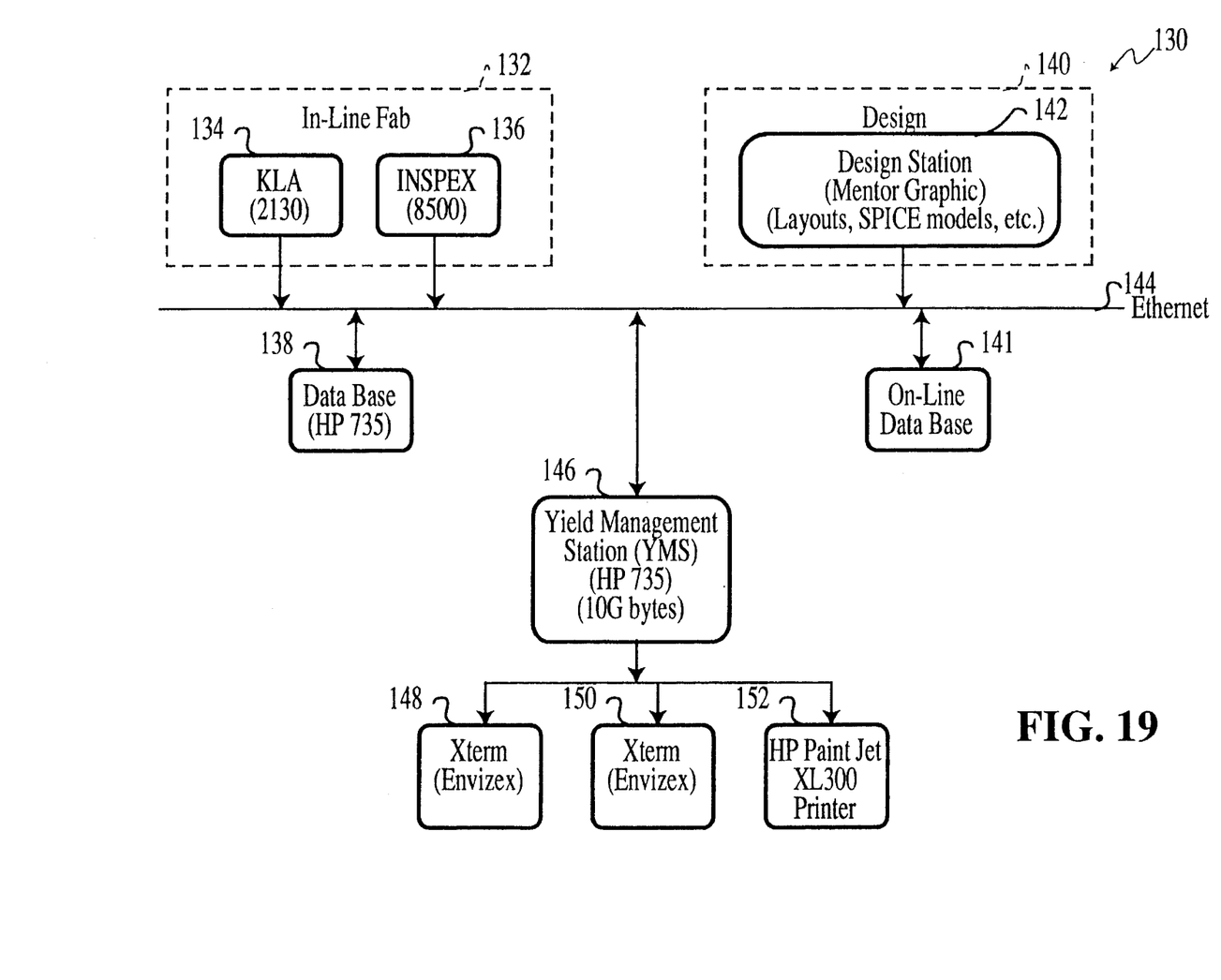
FIG. 19 is a block diagram illustrating the real-time in-line defect disposition and yield forecasting system.

FIG. 19 is a block diagram of the equipment in the real-time in-line defect disposition and yield forecasting system. As shown in FIG. 19, the real-time in-line defect disposition and yield forecasting system 130 includes standard in-line fabrication equipment 132 which collects the different particle sizes and locations of the particle sizes with respect to different layers in a semiconductor wafer. For example, the in-line fabrication equipment KLA 2130 manufactured by KLA Company in Sunnyvale, Calif. identified by reference numeral 134, or the INSPEX 8500 fabrication equipment manufactured by INSPEX Company in Boston, Mass. identified by reference numeral 136 may be used. The collected data is then transmitted via Ethernet drive transmission line 144 to data base 138. For example, the Hewlett Packard 735 computer includes such a function of collecting the data output from the in-line fabrication equipment 132 and storing for later retrieval.

In addition, the defect disposition and yield forecasting system 130 also includes standard design station equipment 140 such as the design equipment 142 manufactured by Mentor Graphics in Oregon. Design station 142 is able to extract the various layouts for each layer in the semiconductor wafer as previously discussed. These layouts are then stored in data base 141 via Ethernet driven transmission line 144. The particle size and locations stored in data base 138 and the layout information stored in database 141 are then collected by the yield management station (YMS) 146 to determine the number and location of actual defects, as well as the defect sensitive area index for each of the layers in the semiconductor wafer under examination. Yield management station 146 can be, for example, Hewlett Packard's 735 computer with preferably 10 gigabytes of hard disk memory storage. The particle size, and location information and layout information are then analyzed as described in connection with FIGS. 17–18, the results of which are then displayed on monitors 148 and 150 or printed on printer 152. Examples of monitors 148 and 150 are the Exterm Display manufactured by Envizex. An example of the printer 152 is the Hewlett Packard Paint Jet XL300 printer.

Accordingly, the real-time in-line defect disposition and yield forecasting system is able to determine the number of actual defects caused for each layer of a semiconductor wafer, and is also able to determine the defect sensitive area index for each layer of the semiconductor wafer. Using this detailed information, the real-time in-line defect disposition and yield forecasting system is able to accurately determine the status or condition of each layer of the semiconductor wafer to determine the layer which has the highest yield probability or possibility after inspection and analysis. Accordingly, the defect disposition and yield forecasting system is able to efficiently and effectively determine which layer of a semiconductor wafer requires inspection and analysis to correct device defects. The defect disposition and yield forecasting system is therefore also able to optimize the amount of device defects which may be corrected for different layers in a semiconductor wafer.

The many features and advantages of the invention are apparent from the detailed specification, and thus, it is intended by the appended claims to cover all such features and advantages of the invention which fall within the true spirit and scope of the invention. Further, since numerous modifications and variations will readily occur to those skilled in the art, we do not desire to limit the invention to the exact construction and operation illustrated and described. Accordingly, all suitable modifications and equivalents may be resorted to, falling within the scope of the invention.

What is claimed is:

1. A real-time in-line defect disposition and yield forecasting system for a semiconductor wafer having layers containing devices, comprising:

an in-line fabrication inspection tool inspecting at least two layers of the semiconductor wafer and producing first information including particle size, particle location and number of particles introduced therein for each of the at least two layers;

a design review station inspecting the at least two layers of the semiconductor wafer and producing second information including layouts of each of the at least two layers; and a yield management station, operatively connected to said in-line fabrication inspection tool and to said design review station, retrieving the first information and the second information, determining at least one of a number of killer defects for the devices in each of the at least two layers and a defect sensitive area index for each of the at least two layers responsive to the first and second information, and further determining a priority for analyzing each of the at least two layers responsive to at least one of the number of killer defects and the defect sensitive area index for each of the at least two layers.

2. A real-time in-line defect disposition and yield forecasting system according to claim 1, wherein said yield management station determines (1) initial sensitive areas for each of the at least two layers responsive to the second information and a reference particle size, and (2) sensitive areas for each of the at least two layers responsive to the initial sensitive areas and the particle size for each of the at least two layers.

3. A real-time in-line defect disposition and yield forecasting system according to claim 1, wherein:

(1) said yield management station determines sensitive areas for each of the at least two layers responsive to the layouts and the particle size for each of the at least two layers, and (2) the defect sensitive area index is determined for each of the at least two layers responsive to the sensitive areas and the particle size.

4. A real-time in-line defect disposition and yield forecasting system according to claim 1, wherein the at least two layers are located in different semiconductor wafers.

5. A real-time in-line defect disposition and yield forecasting system according to claim 1, wherein said yield management station determines that a first layer of the at least two layers is of higher priority when the first layer has a higher number of killer defects and a higher defect sensitive area index than a remaining layer of the at least two layers.

6. A real-time in-line defect disposition and yield forecasting system according to claim 1, wherein said yield management station determines (1) sensitive areas for each of the at least two layers responsive to the layouts and the particle size for each of the at least two layers, and (2) that a first layer of the at least two layers is of higher priority when the first layer has a higher total defect sensitive area and a higher defect sensitive area index than a remaining layer of the at least two layers.

7. A real-time in-line defect disposition and yield forecasting system according to claim 1, wherein said yield management station determines (1) sensitive areas for each of the at least two layers responsive to the layouts and the particle size for each of the at least two layers, and (2) that a first layer of the at least two layers is of higher priority when the first layer has a higher total defect sensitive area and a higher number of particles than a remaining layer of the at least two layers.

8. A real-time in-line defect disposition and yield forecasting system according to claim 1, wherein said yield management station determines (1) sensitive areas for each of the at least two layers responsive to the layouts and the particle size for each of the at least two layers, and (2) that a first layer of the at least two layers is of higher priority when the first layer has a higher total defect sensitive area and a higher number of killer defects than a remaining layer of the at least two layers.

9. A real-time in-line defect disposition and yield forecasting system according to claim 1, wherein said yield management station determines that a first layer of the at least two layers is of higher priority when the first layer has a higher number of killer defects and a higher number of particles than a remaining layer of the at least two layers.

10. A real-time in-line defect disposition and yield forecasting system according to claim 1, wherein said yield management station determines (1) sensitive areas for each of the at least two layers responsive to the layouts and the particle size for each of the at least two layers, and (2) that a first layer of the at least two layers is of higher priority when the first layer has at least two of a higher total defect sensitive area, a higher number of particles, a higher number of killer defects, and a higher defect sensitive area index than a remaining layer of the at least two layers.

11. A real-time in-line defect disposition and yield forecasting system according to claim 1, wherein said yield management station determines (1) sensitive areas for each of the at least two layers responsive to the layouts and the particle size for each of the at least two layers, and (2) that a first layer of the at least two layers is of higher priority when the first layer has at least three of a higher total defect sensitive area, a higher number of particles, a higher number of killer defects, and a higher defect sensitive area index than a remaining layer of the at least two layers.

12. A real-time in-line defect disposition and yield forecasting system for a semiconductor wafer having layers each with devices, comprising:

an in-line fabrication inspection tool inspecting at least two layers of the semiconductor wafer and producing first information including particle size, particle location and number of particles introduced therein for each of the at least two layers;

a design review station inspecting the at least two layers of the semiconductor wafer and producing second information including layouts of each of the at least two layers; and yield management means, operatively connected to said in-line fabrication inspection tool and to said design review station, for retrieving the first information and the second information, determining at least one of a number of killer defects for the devices in each of the at least two layers and a defect sensitive area index for each of the at least two layers responsive to the first and second information, and determining a priority for analyzing each of the at least two layers responsive to at least one of the number of killer defects and the defect sensitive area index for each of the at least two layers.

13. A real-time in-line defect disposition and yield forecasting system for a semiconductor wafer having layers each with devices, comprising:

first inspection means for inspecting at least two layers of the semiconductor wafer and for producing first information including particle size, particle location and number of particles introduced therein for each of the at least two layers;

second inspection means for inspecting the at least two layers of the semiconductor wafer and for producing second information including layouts of each of the at least two layers; and third means, operatively connected to said in-line fabrication inspection tool and to said design review station, for retrieving the first information and the second information, determining at least one of a number of killer defects for the devices in each of the at least two layers and a defect sensitive area index for each of the at least two layers responsive to the first and second information, and determining a priority for analyzing each of the at least two layers responsive to at least one of the number of killer defects and the defect sensitive area index for each of the at least two layers.

14. A real-time in-line defect disposition and yield forecasting method for a semiconductor wafer having layers each with devices, said method comprising the steps of:

(a) inspecting at least two layers of the semiconductor wafer and producing first information including particle size, particle location and number of particles introduced therein for each of the at least two layers;

(b) inspecting the at least two layers of the semiconductor wafer and producing second information including layouts of each of the at least two layers;

(c) retrieving the first information produced by said inspecting step (a) and the second information produced by said inspecting step (b);

(d) determining at least one of a number of killer defects for the devices in each of the at least two layers and a defect sensitive area index for each of the at least two layers responsive to the first and second information; and (e) determining a priority for analyzing each of the at least two layers responsive to at least one of the number of killer defects and the defect sensitive area index for each of the at least two layers.

15. A real-time in-line defect disposition and yield forecasting method according to claim 14, wherein said method further comprises the steps of:

(1) determining sensitive areas for each of the at least two layers responsive to the layouts and the particle size for each of the at least two layers, and (2) determining that a first layer of the at least two layers is of higher priority when the first layer has at least two of a higher total defect sensitive area, a higher number of particles, a higher number of killer defects, and a higher defect sensitive area index than a remaining layer of the at least two layers.

16. A real-time in-line defect disposition and yield forecasting method for a semiconductor wafer having layers each with devices, said method comprising the steps of:

(a) inspecting at least two layers of the semiconductor wafer and producing first information including particle characteristics, the particle characteristics including particle size, particle location and number of particles and second information including layouts for each of the at least two layers;

(b) determining at least one of a number of killer defects for the devices in each of the at least two layers and a defect sensitive area index for each of the at least two layers responsive to the first and second information; and (c) determining a priority for analyzing each of the at least two layers responsive to at least one of the number of killer defects and the defect sensitive area index for each of the at least two layers.

17. A real-time in-line defect disposition and yield forecasting method for a semiconductor wafer having layers each with devices, said method comprising the steps of:

(a) inspecting at least two layers of the semiconductor wafer and determining at least one of a number of killer defects for the devices and a defect sensitive area index for each of the at least two layers responsive to particle size, particle location, number of particles and device layouts in the at least two layers; and (b) determining a priority for analyzing each of the at least two layers responsive to at least one of the number of killer defects and the defect sensitive area index for each of the at least two layers, and analyzing at least one of the at least two layers in accordance with the determined priority.

* * * * *